United States Patent [19]

Schwarz et al.

[11] Patent Number: 5,014,707
[45] Date of Patent: May 14, 1991

[54] APPARATUS FOR MEASURING AND EVALUATING THE INHERENT FLUORESCENT SPECTRA OF ORGANIC TISSUE SURFACES

[75] Inventors: Jürgen Schwarz, Oberkochen; Wolfgang Lohmann, Giessen, both of Fed. Rep. of Germany

[73] Assignee: Carl-Zeiss-Stiftung, Heidenheim, Fed. Rep. of Germany

[21] Appl. No.: 348,417

[22] Filed: May 8, 1989

[30] Foreign Application Priority Data

May 7, 1988 [DE] Fed. Rep. of Germany ....... 3815743

[51] Int. Cl.⁵ .................. A61B 6/08; G01N 21/64
[52] U.S. Cl. .................. 128/633; 250/461.1; 250/461.2; 356/318
[58] Field of Search ............... 356/317, 318; 351/221; 250/458.1, 459.1, 461.1, 461.2; 128/633, 665

[56] References Cited

U.S. PATENT DOCUMENTS

| | | | |
|---|---|---|---|
| 4,342,905 | 8/1982 | Fujii et al. | 250/201 |
| 4,617,467 | 10/1986 | Senftle et al. | 250/461.2 |
| 4,758,081 | 7/1988 | Barnes | 351/221 |
| 4,852,987 | 8/1989 | Lohmann | 351/221 |

OTHER PUBLICATIONS

"Laser-Scanning-Mikroskop mit Automatischer Fokussierung", by W. Deinet, M. Linke, R. Müller and I. Sander, Microscopica Acta, vol. 87, No. 2, Mar. 1983, pp. 129-138, S. Hirzel Verlag 1983.

Primary Examiner—Vincent P. McGraw
Attorney, Agent, or Firm—Walter Ottesen

[57] ABSTRACT

The invention relates to a modified microscope-photometer which makes it possible to record and evaluate inherent fluorescent spectra of organic tissue surfaces. The modified microscope-photometer affords the advantage of being able to illuminate the object in a path coaxial to the viewing direction.

2 Claims, 5 Drawing Sheets

APPARATUS FOR MEASURING AND EVALUATING THE INHERENT FLUORESCENT SPECTRA OF ORGANIC TISSUE SURFACES

FIELD OF THE INVENTION

The invention relates to an apparatus for measuring and evaluating inherent fluorescent spectra of organic tissue surfaces for which the stimulating wavelength $\lambda_4$ lies in the range between 320 nm and 550 nm. An evaluation device determines the maximum intensity of the reflected light at the wavelength $\lambda_4$ and determines the maximum intensity of the fluorescent light in the range of wavelengths longer than $\lambda_4$.

BACKGROUND OF THE INVENTION

An apparatus of the kind described above is disclosed in U.S. Pat. No. 4,852,987 incorporated herein by reference.

The known apparatus uses as a light source the projection of a slit image onto the organic tissue surface to be investigated.

SUMMARY OF THE INVENTION

It is an object of the invention to provide an apparatus for the above purpose which permits a surface illumination of the object to be investigated.

The advantages obtained with the invention are especially seen in that the modular parts of a known apparatus can be used whereby cost of a new production series can be saved. It is an advantage of the invention to utilize the modular parts of a known microscope commercially available under the name AXIOTRON. A further advantage of the invention is the illumination of the object coaxial to the viewing direction.

BRIEF DESCRIPTION OF THE DRAWINGS

The invention will now be explained with reference to the drawings wherein.

DESCRIPTION OF THE PREFERRED EMBODIMENTS OF THE INVENTION

Figure 1:
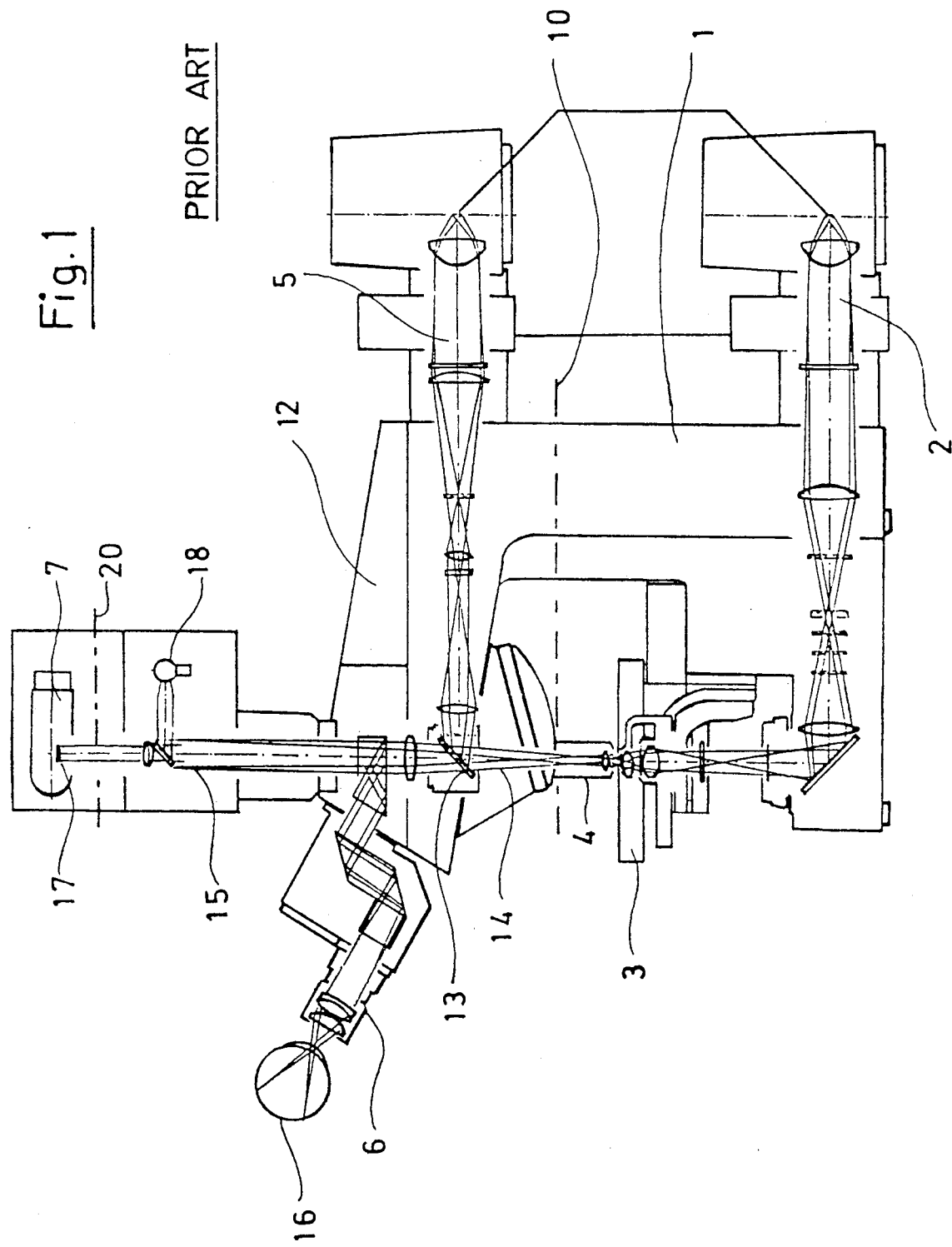
FIG. 1 is a schematic of a microscope-photometer of known configuration which is available in the marketplace under the name AXIOTRON and is a product of Carl Zeiss, a company organized and doing business in the Federal Republic of Germany.

Referring to FIG. 1, the microscope-photometer shown includes a microscope stand 1. Reference numeral 2 identifies the subsurface illumination device and reference numeral 6 identifies the ocular tube. The eye of a viewer is identified by reference numeral 16. The microscope-photometer includes an object stage 3 and an objective 4 as well as an incident illuminating device 5 having an illumination beam which is reflected into the viewing beam path 14 of the microscope-photometer via a divider plate 13. Reference numeral 15 identifies a photometer measurement diaphragm mounted in an intermediate image plane and reference numeral 18 identifies an ancillary light source for illuminating this measurement diaphragm. Reference numeral 17 identifies the pupillary plane of a photo cathode 7.

Reference numeral 10 identifies a first interface location which separates the stand 1 and the objective tube 4 mechanically at this location such that an objective can be inserted which is suitable for measuring and evaluating inherent fluorescence of organic tissue surfaces. A second interface location is identified by reference numeral 20 and makes possible the attachment of a spectrograph or a light-conducting shape converter. The light-conducting shape converter converts a circularly-shaped field of view into a rectangular field of view and leads to a spectrograph.

Figure 2:
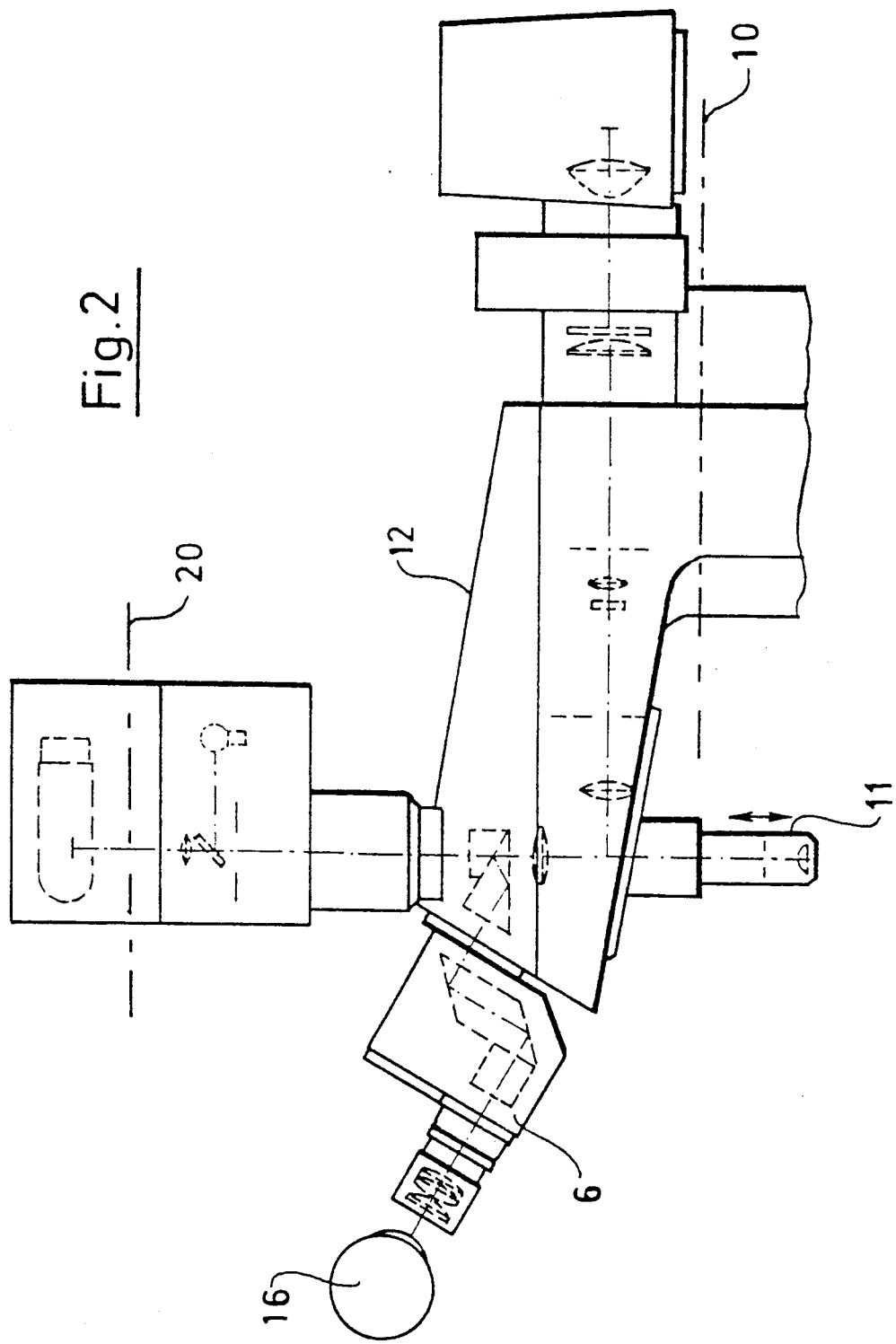
FIG. 2 is a schematic of the upper portion of the microscope-photometer of FIG. 1 modified according to the invention.

In the schematic of FIG. 2, the trunk portion 12 of the microscope-photometer is shown which remains after removal of the portion thereof lying beneath the interface location 10 and above the interface location 20.

Figure 3:
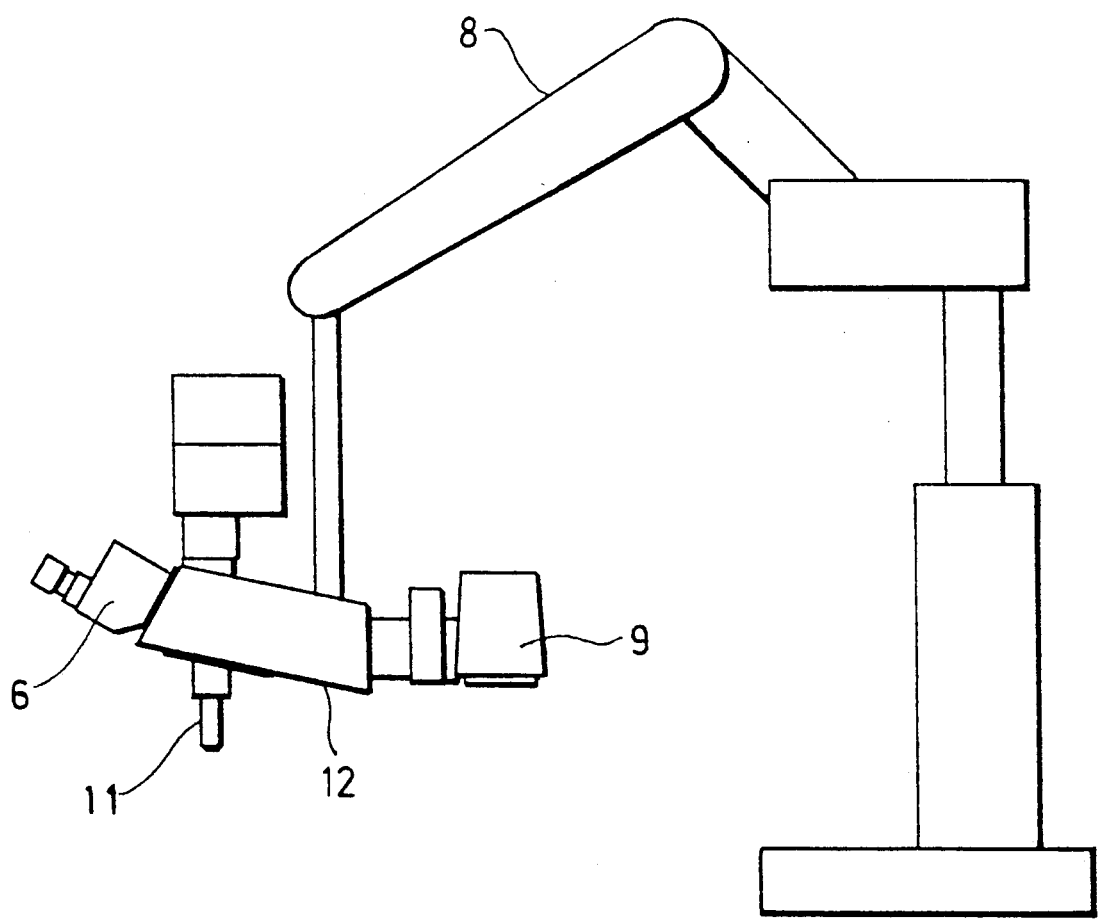
FIG. 3 is a schematic of the microscope-photometer of FIG. 2 shown mounted on a floor stand.

In FIG. 3, the upper trunk 12 is shown attached to a floor stand 8 which has a freely movable arm and is equipped with a tilting and pivoting device. This floor stand is known per se. In lieu of the floor stand, a suitable known wall or ceiling attachment can be utilized.

Figure 4:
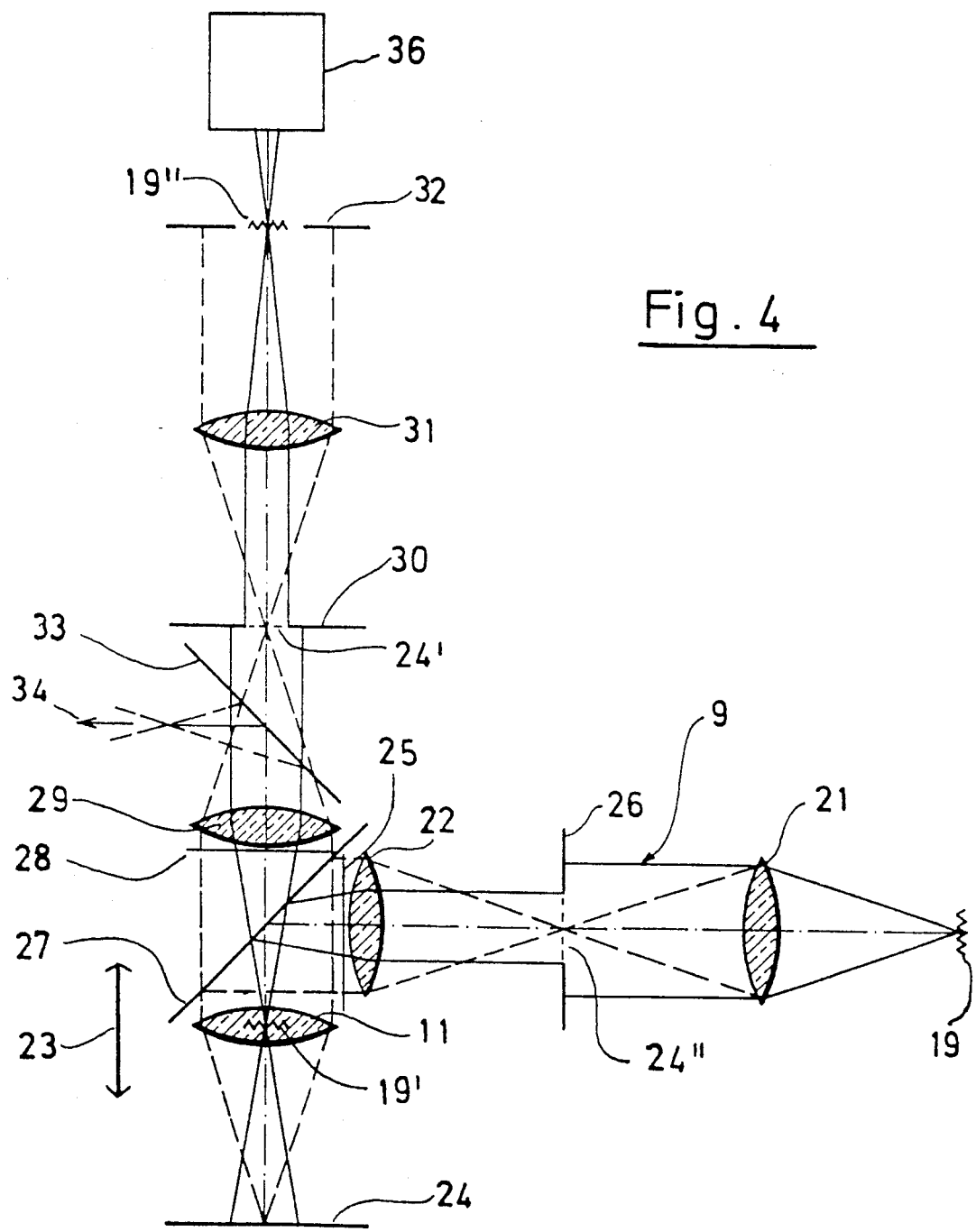
FIG. 4 is a schematic showing the beam path in a microscope-photometer modified according to the invention; and, FIG. 5 is a fragmentary view showing a light-conducting shape converter interposed ahead of the spectrograph.

In the schematic of FIG. 4, reference numeral 19 identifies a light source of known configuration suitable for making recordings of inherent fluorescent spectra. The light source 19 can, for example, be an HBO lamp commercially available from the Osram Company organized and doing business in the Federal Republic of Germany. Reference numerals 21 and 22 identify condenser lenses for imaging the light source 19 into the plane 19' of the objective 11. The illumination device 9 generates light to stimulate fluorescence at the surface of the object 24 at a stimulating wavelength $\lambda_4$ which is freely selectable in the range of 250 nm to 550 nm.

The objective 11 is capable of transmitting light in the ultra-violet wavelength range and is movable in the vertical direction as indicated by double arrow 23 so that it can be focused. Suitable focusing mechanisms are disclosed, for example, in U.S. Pat. No. 4,342,905 and in the article entitled "Laser-Scanning-Mikroskop mit automatischer Fokussierung" by W. Deinet et al, MICROSCOPICA ACTA, Volume 87, Number 2, Pages 129-138, March 1983.

Referring still to FIG. 4, reference numeral 24 identifies the object which has a reflecting and fluorescent surface. A fluorescence stimulating filter 25 is arranged in the illuminating beam path. A field diaphragm 26, which is disposed in an image plane 24" of the object 24 is also arranged in the illuminating beam path. The fluorescent light transmitted from the object passes through a color divider 27 and into the entrance slit 32 of a spectrograph 36 via an absorbing filter 28, which can be pivoted into and out of the beam path, and the tube lens 29 and then through a measurement diaphragm 30 mounted in the first object image plane 24' and then via a relay lens 31. The spectrograph 36 is provided at interface 20 and detects the backscattered light from the surface of the object in the wavelength range between 250 nm and 700 nm.

Figure 5:
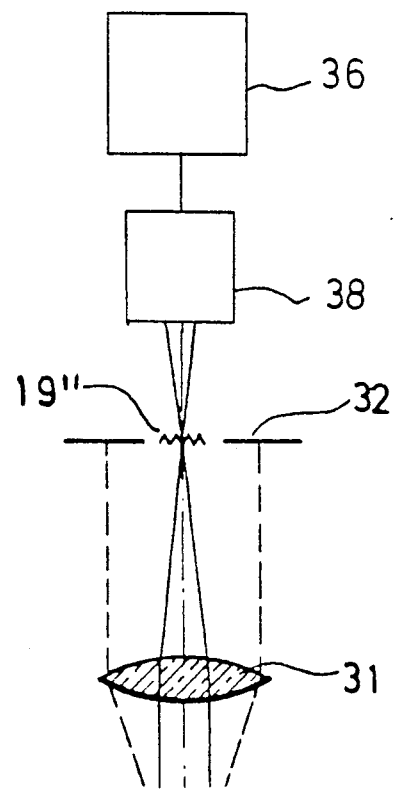

Alternatively, and after passing into the entrance slit 32, the fluorescent light can reach a light-conducting shape converter 38 which, in turn, leads to the spectrograph 36 as shown in FIG. 5. The entrance slit 32 is arranged in the second image plane 19" of the light source 19. Light transmitted from the object can reach a viewing device lying in the direction of arrow 34 such as an ocular tube via a switchable mirror 33.

The spectrograph 36 and light-conducting shape converter 38 are available in the marketplace. For example, a suitable spectrograph is available from EG & G, Princeton Applied Research, Princeton, N.J., United States of America, (Detector 1420 BR 1024) and a suitable shape converter is also available from said EG & G, Princeton Applied Research.

In lieu of the objective 11, a rigid endoscope can be provided.

It is understood that the foregoing description is that of the preferred embodiments of the invention and that various changes and modifications may be made thereto without departing from the spirit and scope of the invention as defined in the appended claims.

What is claimed is:

1. In an arrangement for measuring and evaluating the inherent fluorescent spectra of the surface of an object defining an object plane, the object being in the form of an organic tissue specimen of a patient, the arrangement including: an evaluation device for determining the maximum intensity of the light reflected from said surface at a wavelength $\lambda_4$ and for determining the maximum intensity of the fluorescent light from said surface in the range of wavelengths longer than $\lambda_4$; and, a modified microscope photometer for illuminating the surface of the specimen and for transmitting the light from said surface to said evaluation device, the modified microscope photometer comprising:

a housing;

a stand for mounting said housing thereon;

movable structure means interposed between said stand and said housing for facilitating the movement of said housing with respect to the patient so as to place said housing next to said object;

illuminating light source means mounted in said housing for generating light at said wavelength $\lambda_4$ of between 250 nm and 550 nm;

imaging means for imaging said light source onto said object to stimulate the inherent fluorescence of the organic tissue of the object;

said imaging means including an objective for imaging an object plane and defining an optical axis transverse to said object plane;

said objective being capable of transmitting light in the ultra-violet wavelength range and being mounted on said optical axis so as to be movable relative to said object for focussing the reflected and fluorescent light from the latter and transmitting the same down said optical axis; and, a spectrograph operatively connected to said evaluation device and mounted on said optical axis for detecting said light from said object in a wavelength range of 250 nm and 700 nm.

2. The modified microscope photometer of claim 1, comprising a light-conductor shape converter interposed ahead of said spectrograph.

* * * * *